United States Patent
Tanaka et al.

(10) Patent No.: US 6,852,890 B1
(45) Date of Patent: Feb. 8, 2005

(54) PROCESS FOR THE PREPARATION OF PHENYLHYDRAZINES

(75) Inventors: Kazuyuki Tanaka, Ibaraki (JP); Yoshiaki Oda, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/959,661

(22) PCT Filed: Mar. 3, 2000

(86) PCT No.: PCT/JP00/01261
§ 371 (c)(1),
(2), (4) Date: Nov. 2, 2001

(87) PCT Pub. No.: WO01/66513
PCT Pub. Date: Sep. 13, 2001

(51) Int. Cl.$^7$ ............................................. C07C 241/02
(52) U.S. Cl. ...................................................... 564/314
(58) Field of Search ......................................... 564/314

(56) References Cited

U.S. PATENT DOCUMENTS

| | | |
|---|---|---|
| 3,410,900 A | 11/1968 | Kindler et al. |
| 4,042,373 A | 8/1977 | Moje |
| 5,599,992 A | 2/1997 | Arndt |
| 6,057,478 A | 5/2000 | Schach et al. |
| 6,087,534 A | 7/2000 | Mas et al. |

FOREIGN PATENT DOCUMENTS

| | | |
|---|---|---|
| EP | 0 206 435 | 12/1986 |
| EP | A 0 959 067 | 11/1999 |
| FR | A1 331 187 | 12/1996 |
| JP | 63-41448 A | 2/1988 |

OTHER PUBLICATIONS

Muller, XP002151816, pp. 1180–1191 (1967).
Preston et al., Journal of the Chemical Soctiety, XP000960306, p. 2461 (1928).
G. H. Coleman, Orangic Syntheses Collective vol. 1, 442–445 (1941).

*Primary Examiner*—Samuel Barts
(74) *Attorney, Agent, or Firm*—Birch, Stewart, Kolasch & Birch, LLP

(57) ABSTRACT

A process for the preparation of a phenylhydrazine or an inorganic acid salt thereof of the formula (1):

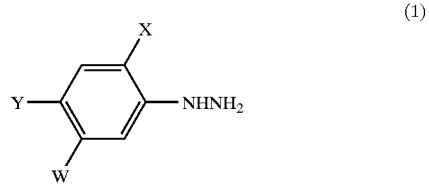

(1)

wherein X is a hydrogen or halogen atom; Y is a halogen atom; and W is a hydrogen atom or —ZR in which Z is an oxygen or sulfur atom, and R is a hydrogen atom, an alkyl group, a haloalkyl group, and so on, by the hydrolysis of a phenylhydrazine derivative of the formula (2):

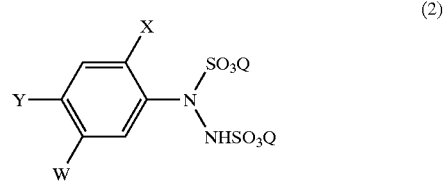

(2)

where X, Y and W are the same as defined above, and the Q groups are a hydrogen atom, an ammonium group or an alkali metal atom in the presence of water and an inorganic acid, in which the concentration of the inorganic acid is at least 6 moles per 1 kg of water in a reaction system.

6 Claims, No Drawings

PROCESS FOR THE PREPARATION OF PHENYLHYDRAZINES

BACKGROUND OF THE INVENTION

1. Field of the Invention

The present invention relates to a process for the preparation of a phenylhydrazine or an inorganic acid salt thereof of the formula (1):

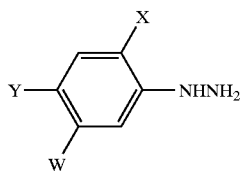

(1)

wherein X is a hydrogen atom or a halogen atom; Y is a halogen atom; and W is a hydrogen atom or —ZR in which Z is an oxygen atom or a sulfur atom, and R is a hydrogen atom, a $C_1$–$C_6$ alkyl group, a $C_1$–$C_6$ haloalkyl group, a $C_3$–$C_8$ cycloalkyl group, a benzyl group, a $C_3$–$C_6$ alkenyl group, a $C_3$–$C_6$ haloalkenyl group, a $C_3$–$C_6$ alkynyl group, a cyano-$C_1$–$C_6$ alkyl group, a $C_2$–$C_8$ alkoxyalkyl group, a $C_2$–$C_8$ alkylthioalkyl group, a carboxy-$C_1$–$C_6$ alkyl group, ($C_1$–$C_8$ alkoxy) carbonyl-$C_1$–$C_6$ alkyl group, a [($C_1$–$C_4$ alkoxy)-$C_1$–$C_4$ alkoxy]carbonyl-$C_1$–$C_6$ alkyl group, ($C_3$–$C_8$ cycloalkoxy)carbonyl -$C_1$–$C_6$ alkyl group or a [($C_1$–$C_6$ alkoxy)carbonyl-$C_1$–$C_6$ alkyl]oxycarbonyl-$C_1$–$C_6$ alkyl group.

A phenylhydrazine of the formula (1) is a useful intermediate for the preparation of, for example, pyridazin-3-on compounds of the formulae (4):

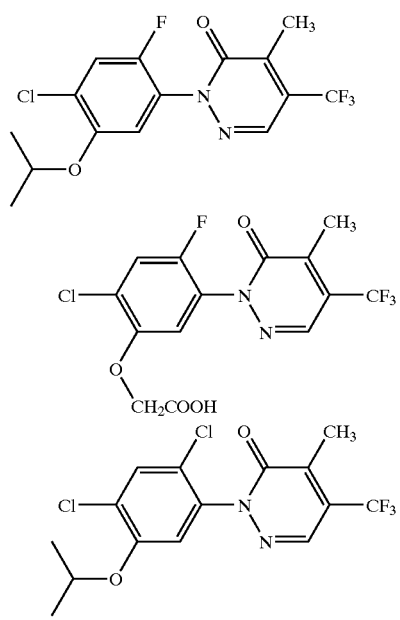

(4)

which have good herbicidal activities.

2. Prior Art

JP-A-9-323977 describes that a phenylhydrazine of the above formula (1) is synthesized by diazotizing an aniline derivative of the formula (3):

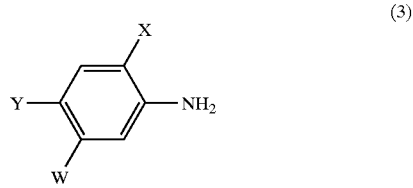

(3)

wherein X, Y and W are the same as defined above, and then reducing the diazotized compound with tin chloride.

However, the above synthesis process has drawbacks such that a reaction mixture has low filterability when insoluble tin-containing by-products are removed by filtration after the reaction, since the reduction is performed with tin chloride, and that tin compounds should be treated after the reaction. Therefore, such a synthesis process may not be industrially preferred. Thus, it is highly desired to develop a new synthesis process of a phenylhydrazine or an inorganic acid salt thereof of the formula (1) using no metal reducing agents.

SUMMARY OF THE INVENTION

Extensive studies have been made to solve the drawbacks of the conventional synthesis process. As a result, it has been found that a phenylhydrazine or an inorganic acid salt thereof of the formula (1) is advantageously obtained by hydrolyzing a phenylhydrazine derivative of the following formula (2) by allowing the phenylhydrazine derivative in contact with an inorganic acid in a concentration of at least 6 moles of the inorganic acid per 1 kg of water in a reaction system, and furthermore dehalogenated by-products can be efficiently reduced.

Accordingly, the present invention provides a process for the preparation of a phenylhydrazine or an inorganic acid salt thereof of the formula (1):

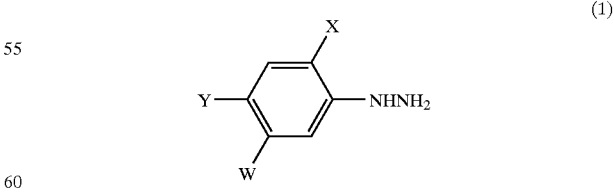

(1)

wherein X is a hydrogen atom or a halogen atom; Y is a halogen atom; and W is a hydrogen atom or —ZR in which Z is an oxygen atom or a sulfur atom, and R is a hydrogen atom, a $C_1$–$C_6$ alkyl group, a $C_1$–$C_6$ haloalkyl group, a $C_3$–$C_6$ cycloalkyl group, a benzyl group, a $C_3$–$C_6$ alkenyl group, a $C_3$–$C_6$ haloalkenyl group, a $C_3$–$C_6$ alkynyl group, a cyano-$C_1$–$C_6$ alkyl group, a $C_2$–$C_8$ alkoxyalkyl group, a $C_2$–$C_8$ alkylthioalkyl group, a carboxy-$C_1$–$C_6$ alkyl group, ($C_1$–$C_8$ alkoxy)carbonyl-$C_1$–$C_6$, alkyl group, a [($C_1$–$C_4$ alkoxy)-$C_1$–$C_4$ alkoxy]carbonyl-$C_1$–$C_6$ alkyl group, ($C_3$–$C_8$ cycloalkoxy)carbonyl-$C_1$–$C_6$ alkyl group or a [($C_1$–$C_6$ alkoxy) carbonyl-$C_1$–$C_6$ alkyl]oxycarbonyl-$C_1$–$C_6$ alkyl group comprising the step of hydrolyzing a phenylhydrazine derivative of the formula (2):

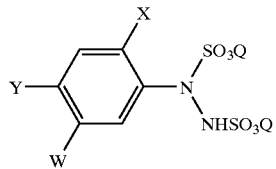

(2)

wherein X, Y and W are the same as defined above, and the Q groups are the same or different and represent a hydrogen atom, an ammonium group or an alkali metal atom in the presence of water and an inorganic acid, wherein the concentration of the inorganic acid is at least 6 moles per 1 kg of water in a reaction system.

DETAILED DESCRIPTION OF THE INVENTION

Herein, a halogen atom for X and Y may be a fluorine atom, a chlorine atom, a bromine atom or an iodine atom.

Examples of a $C_1$–$C_6$ alkyl group for R include a methyl group, an ethyl group, an isopropyl group, a propyl group, an isobutyl group, a tert.-butyl group, an amyl group, an isoamyl group, a tert.-amyl group, etc.

Examples of a $C_1$–$C_6$ haloalkyl group include a 2,2,2-trifluoroethyl group, etc.

Examples of a $C_3$–$C_8$ cycloalkyl group include a cyclopropyl group, a cyclobutyl group, a cyclopentyl group, a cyclohexyl group, etc.

Examples of a $C_3$–$C_6$ alkenyl group include an allyl group, a 1-methyl-2-propenyl group, a 3-butenyl group, a 2-butenyl group, a 3-methyl-2-butenyl group, a 2-methyl-3-butenyl group, etc.

Examples of a $C_3$–$C_6$ haloalkenyl group include a 2-chloro-2-propenyl group, a 3,3-dichloro-2-propenyl group, etc.

Examples of a $C_3$–$C_6$ alkynyl group include a propargyl group, a 1-methyl-2-propynyl group, a 2-butynyl group, a 1,1-dimethyl-2-propynyl group, etc.

Examples of a cyano-$C_1$–$C_6$ alkyl group preferably include a $C_1$–$C_6$ cyanoalkyl group such as a cyanomethyl group, etc.

Examples of a $C_2$–$C_8$ alkoxyalkyl group include a methoxyethyl group, an ethoxymethyl group, an ethoxyethyl group, etc.

Examples of a $C_2$–$C_8$ alkylthioalkyl group include a methylthioethyl group, etc.

Examples of a carboxy-$C_1$–$C_6$ alkyl group include a carboxymethyl group, a 1-carboxyethyl group, a 2-carboxyethyl group, etc.

Examples of ($C_1$–$C_6$ alkoxy) carbonyl-$C_1$–$C_6$ alkyl group include a methoxycarbonylmethyl group, an ethoxycarbonylmethyl group, a propoxycarbonylmethyl group, an isopropoxycarbonylmethyl group, a butoxycarbonylmethyl group, an isobutoxycarbonylmethyl group, a tert.-butoxycarbonylmethyl group, an amyloxycarbonylmethyl group, an isoamyloxycarbonylmethyl group, a tert.-amyloxy-carbonylmethyl group, a 1-methoxycarbonylethyl group, a 1-ethoxycarbonylethyl group, a 1-propoxycarbonylethyl group, a 1-isopropoxycarbonylethyl group, a 1-butoxycarbonylethyl group, a 1-isobutoxycarbonylethyl group, a 1-tert.-butoxycarbonylethyl group, a 1-amyloxycarbonylethyl group, a 1-isomyloxycarbony-ethyl group, a 1-tert.-amyloxycarbonylethyl group, etc.

Examples of a [($C_1$–$C_6$ alkoxy)-$C_1$–$C_6$ alkoxy]carbonyl-$C_1$–$C_6$ alkyl group include a methoxyethoxycarbonylmethyl group, a 1-methoxyethoxycarbonylethyl group, etc.

Examples of ($C_3$–$C_8$ cycloalkoxy)carbonyl-$C_1$–$C_6$ alkyl group include a cyclobutyloxycarbonylmethyl group, a cyclopentyloxycarbonylmethyl group, a cyclohexyloxycarbonyl-methyl group, a 1-cyclobutyloxycarbonylethyl group, a 1-cyclopentyloxycarbonylethyl group, a 1-cyclohexyloxycarbonylethyl group, etc.

Examples of a [($C_1$–$C_6$ alkoxy)carbonyl-$C_1$–$C_6$ alkyl] oxy-carbonyl-$C_1$–$C_6$ alkyl group include an (ethoxycarbonyl)methoxy-carbonylmethyl group, etc.

Examples of an alkali metal atom for Q include a sodium atom, a potassium atom, etc.

A phenylhydrazine derivative of the formula (2) may be prepared by diazotizing an aniline derivative of the formula (3) and then reacting the obtained diazonium salt with sulfurous acid, a sulfite salt or a hydrogensulfite salt.

A diazotizing agent used in the above preparation method is usually a nitrite salt. Examples of a nitrite salt include sodium nitrite, potassium nitrite, etc. A nitrite salt is usually used in the form of an aqueous solution, although a nitrite salt in a solid form may be used. The amount of a nitrite salt is usually from 1 to 1.2 moles per one mole of an aniline derivative of the formula (3).

In general, an inorganic acid is used in the diazotizing reaction. Examples of an inorganic acid include hydrochloric acid, sulfuric acid, phosphoric acid, nitric acid, etc. Preferably, hydrochloric acid and sulfuric acid are used. Usually, an inorganic acid is used in the form of an aqueous solution.

The amount of an inorganic acid is about 1 to 10 moles, preferably about 2 to 6 moles, more preferably about 2.5 to 4 moles, per one mole of an aniline derivative of the formula (3).

In the diazotizing reaction, the order of the addition of reagents is not limited. Usually, an aniline derivative is mixed with the aqueous solution of an inorganic acid, and then the aqueous solution of a nitrite salt is added thereto.

A reaction temperature is usually from about −20 to 20° C., preferably from about −10 to 100, more preferably from about −5 to 5° C.

Examples of a sulfite salt used as a reducing agent include ammonium sulfite, sodium sulfite, potassium sulfite, etc. Examples of a hydrogensulfite salt include ammonium hydrogensulfite, sodium hydrogensulfite, potassium hydrogensulfite, etc. They are usually used in the form of an aqueous solution, although they may be used in a solid form.

The amount of sulfurous acid, a sulfite salt or a hydrogensulfite salt is usually at least 2 moles, preferably from about 2.5 to 4 moles, per one mole of an aniline derivative of the formula (3).

pH of the reaction system is adjusted usually in the range between 5.5 and 8, preferably in the range between 6 and 7.5. The pH of the reaction system can be adjusted with acids (e.g. hydrochloric acid, sulfuric acid, etc.), or aqueous solutions of alkali compounds (e.g. sodium hydroxide, potassium hydroxide, ammonia, etc.).

In the above reaction, a diazonium salt, which has been obtained by diazotizing an aniline derivative of the formula (3), is added to an aqueous solution containing sulfurous acid, a sulfite or a hydrogensulfite, pH of which is adjusted in the range between 5.5 and 8. A reaction temperature is usually from about 0 to 80° C., preferably from about 10 to 70° C.

A reaction time varies with other conditions such as kinds and amounts of reagents, a reaction temperature, and the like, and cannot be unconditionally limited. The reaction time is usually from about 30 minutes to about 24 hours.

After the termination of the reaction, the obtained reaction mixture is filtered, and thus a hydrophobic phenylhydrazine derivative of the formula (2) is recovered. A water-soluble phenylhydrazine derivative of the formula (2) can be recovered by concentration, or extraction with an organic solvent followed by concentration. Furthermore, the recovered phenylhydrazine derivative can be purified by recrystallization, etc.

The phenylhydrazine derivative of the formula (2) formed in the above-described reaction may be used in the hydrolysis reaction in the presence of an inorganic acid, as it is, in the form of an aqueous solution without being isolated.

Aniline derivatives of the formula (3) are known from, for example, EP-A-61741, U.S. Pat. Nos. 4,670,046, 4,770,695, 4,709,409, 4,640,707, 4,720,927 and 5,169,431, JP-A-63-156787, and the like, or may be prepared by the methods described in these patent publications.

Typical examples of a phenylhydrazine derivative of the formula (2) are listed in Table 1.

TABLE 1

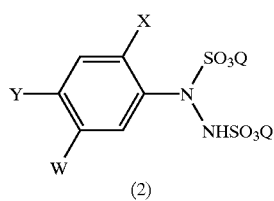

(2)

| Compound No. | X | Y | W | Q |
|---|---|---|---|---|
| 2-1 | H | Cl | H | Na |
| 2-2 | F | Cl | H | Na |
| 2-3 | F | Cl | OH | Na |
| 2-4 | F | Cl | OH | $NH_4$ |
| 2-5 | F | Cl | $OCH(CH_3)_2$ | Na |
| 2-6 | F | Cl | $OCH_2C{\equiv}CH$ | Na |
| 2-7 | F | Cl | $OCH_2COOH$ | Na |
| 2-8 | F | Cl | $SCH_2C{\equiv}CH$ | Na |
| 2-9 | F | Cl | $SCH_2COOH$ | Na |
| 2-10 | Cl | Cl | H | Na |
| 2-11 | Cl | Cl | $OCH(CH_3)_2$ | Na |
| 2-12 | F | Cl | $OCH_3$ | Na |
| 2-13 | F | Cl | $OCH_2CH_3$ | Na |

In the present invention, a phenylhydrazine of the formula (1) can be obtained by hydrolyzing a phenylhydrazine derivative of the formula (2).

The hydrolysis is performed using an inorganic acid. An inorganic acid is preferably a protonic acid such as hydrochloric acid or sulfuric acid. Furthermore, the aqueous solution of an inorganic acid may be used.

An organic solvent may be used together with an inorganic acid, insofar as the organic solvent does not interfere with the hydrolysis.

The amount of an inorganic acid is usually at least 1 mole, preferably from 4 to 50 moles, per one mole of a phenylhydrazine derivative of the formula (2).

The concentration of an inorganic acid is preferably at least 6 moles per 1 kg of water in the reaction system, from the viewpoint of a yield. The concentration of an inorganic acid in the reaction system is preferably set within the prescribed range by taking into account the amount of the inorganic acid and that of water contained in an aqueous solution of the acid and in the phenylhydrazine derivative of the formula (2) or an aqueous solution thereof. The aqueous solution of the phenylhydrazine derivative of the formula (2) may be prepared by dilution with water or by the steps of a diazotization process and subsequent reduction as described above in which various aqueous solutions of reactants as mentioned and water are used.

In the process of the present invention, a phenylhydrazine derivative of the formula (2) or its aqueous solution (or suspension) is added to an inorganic acid or its aqueous solution, although an inorganic acid or its aqueous solution may be added to a phenylhydrazine derivative of the formula (2) or its aqueous solution (or suspension).

Alternatively, the aqueous solution of a phenylhydrazine derivative of the formula (2) is concentrated and then reacted with an inorganic acid.

A reaction temperature in the hydrolysis is usually from −5 to 80° C., preferably from 0 to 50° C.

A reaction time for the hydrolysis varies with other conditions such as kinds and amounts of reagents, a reaction temperature, and the like, and cannot be unconditionally limited. The hydrolysis reaction time is usually from about 30 minutes to about 24 hours.

After the termination of the hydrolysis, the obtained reaction mixture is filtered as it is, or neutralized with an alkaline aqueous solution of, for example, sodium hydroxide, and then filtered. Thus, a phenylhydrazine or an inorganic acid salt thereof of the formula (1) is recovered. The recovered phenylhydrazine or an inorganic acid salt thereof can be purified by recrystallization, etc.

Typical examples of a phenylhydrazine of the formula (1) are listed in Table 2, but the present invention is not limited to those exemplified compounds.

TABLE 2

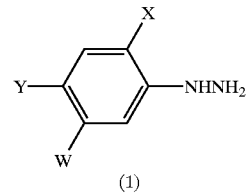

(1)

| Compound No. | X | Y | W |
|---|---|---|---|
| 1-1 | H | Cl | H |
| 1-2 | F | Cl | H |
| 1-3 | F | Cl | $OCH(CH_3)_2$ |
| 1-4 | F | Cl | OH |
| 1-5 | F | Cl | $OCH_2C{\equiv}CH$ |
| 1-6 | F | Cl | $OCH_2COOH$ |
| 1-7 | F | Cl | $SCH_2C{\equiv}CH$ |
| 1-8 | F | Cl | $SCH_2COOH$ |
| 1-9 | Cl | Cl | H |
| 1-10 | Cl | Cl | $OCH(CH_3)_2$ |
| 1-11 | F | Cl | $OCH_3$ |
| 1-12 | F | Cl | $OCH_2CH_3$ |

EFFECTS OF THE INVENTION

According to the present invention, a phenylhydrazine of the formula (1) can be efficiently prepared by hydrolyzing a phenylhydrazine derivative of the formula (2) in the presence of water without the use of any tin compound and without the isolation of the phenylhydrazine derivative from a reaction mixture.

The present invention will be illustrated by following Examples, which do not limit the scope of the present invention in any way.

EXAMPLE 1

4-Chloro-2-fluoro-5-hydroxyaniline (162.0 g; content: 99.6%, 0.999 mole) was added to 10% hydrochloric acid (1093.3 g) at 25° C. while stirring. Then, a 35% aqueous solution of sodium nitrite (205.9 g) was dropwise added to the mixture at a temperature of −3° C. to 0° C. over 1 hour to diazotize 4-chloro-2-fluoro-5-hydroxyaniline to obtain an aqueous solution of a corresponding diazonium salt (1456.7 g).

The diazonium salt was quickly added at 10° C. to an aqueous solution of sodium sulfite, which had been prepared by adding sodium sulfite (398.1 g) to water (1323.2 g) and then adjusting pH of the mixture at 7.2 with 95% sulfuric acid (15.1 g), and the mixture was heated up to 65° C., and maintained at the same temperature for 2 hours. Thus, the aqueous solution (3141.5 g) of sodium 4-chloro-2-fluoro-5-hydroxyphenylhydrazine-N,N'-disulfonate was obtained. According to LC-IS analysis, the yield of this sodium salt was 96.0% based on 4-chloro-2-fluoro-5-hydroxyaniline.

The obtained aqueous solution of disodium 4-chloro-2-fluoro-5-hydroxyphenylhydrazine-N,N'-disulfonate was dropwise added to 35% hydrochloric acid (2913.8 g, 27.97 moles), which corresponds to 28 moles per one mole of 4-chloro-2-fluoro-5-hydroxyaniline, over 2.5 hours while cooling hydrochloric acid at 10° C., and further reacted at the same temperature for 8 hours to obtain a reaction mixture (6048.7 g) (90.0% of 4-chloro-2-fluoro-5-hydroxyphenylhydrazine; 3.1% of the dechlorinated compound (by-product); LC area percentages). After the filtration of the reaction mixture, the residue was dried to obtain a pale pink solid mixture containing 4-chloro-2-fluoro-5-hydroxyphenylhydrazine hydrochloride (438.7 g) (95.6% of 4-chloro-2-fluoro-5-hydroxyphenylhydrazine; 0.3% of the dechlorinated compound (by-product); LC area percentages).

According to LC-IS analysis, the yield of 4-chloro-2-fluoro-5-hydroxyphenylhydrazine was 89.3% based on 4-chloro-2-fluoro-5-hydroxyaniline.

The water content in the reaction system means the total amount of water contained in 10% hydrochloric acid, water contained in the 35% aqueous solution of sodium nitrite, water added to sodium sulfite, water contained in 95% sulfuric acid, and water contained in 35% hydrochloric acid, and it was 4336 g. Thus, the amount of the inorganic acids in the reaction system was 6.5 moles per 1 kg of water.

EXAMPLE 2-1

An aqueous solution (1314.1 g) of disodium 4-chloro-2-fluoro-5-hydroxyphenylhydrazine-N,N'-disulfonate was prepared in the same manner as in Example 1 using 10% hydrochloric acid (437.7 g), 4-chloro-2-fluoro-5-hydroxyaniline (65.0 g; content: 99.6 g; 0.401 mole), a 35% aqueous solution of sodium nitrite (83.1 g), water (539.6 g), sodium sulfite (159.5 g) and 95% sulfuric acid (12.7 g). The obtained aqueous solution was concentrated to 865.9 g by evaporating water at 56° C. under 107 mmHg over 4 hours.

EXAMPLE 2-2

Then, the concentrated aqueous solution (266.4 g) of disodium 4-chloro-2-fluoro-5-hydroxyphenylhydrazine-N,N'-disulfonate was dropwise added to 35% hydrochloric acid (223.5 g, 2.146 moles) over 2.5 hours while cooling hydrochloric acid at 10° C., and further reacted at the same temperature for 9 hours to obtain a reaction mixture (486.5 g) (81.2% of 4-chloro-2-fluoro-5-hydroxyphenylhydrazine; 2.7% of the dechlorinated compound (by-product); LC area percentages). After the filtration of the reaction mixture, the residue was dried to obtain a pale pink solid mixture containing 4-chloro-2-fluoro-5-hydroxyphenylhydrazine hydrochloride (61.9 g) (96.5% of 4-chloro-2-fluoro-5-hydroxyphenylhydrazine; 0.1% of the dechlorinated compound (by-product); LC area percentages).

According to LC-IS analysis, the yield of 4-chloro-2-fluoro-5-hydroxyphenylhydrazine was 89.4% based on 4-chloro-2-fluoro-5-hydroxyaniline.

The water contained in the reaction mixture was 311 g, and thus the amount of the inorganic acids in the reaction system was 6.9 moles per 1 kg of water.

EXAMPLE 3

4-Chloro-2-fluoro-5-hydroxyaniline (20.1 g; content: 99.6%; 0.124 mole) was added to 10% hydrochloric acid (135.8 g) at 25° C. while stirring. Then, a 35% aqueous solution of sodium nitrite (25.9 g) was dropwise added to the mixture at a temperature of −3° C. to 0° C. over 1 hour to diazotize 4-chloro-2-fluoro-5-hydroxyaniline to obtain an aqueous solution of a corresponding diazonium salt (181.7 g).

The diazonium salt was quickly added at 10° C. to a 50% aqueous solution of ammonium hydrogensulfite (73.8 g), pH of which had been adjusted at 7.2 by adding a 30% aqueous solution of sodium hydroxide (41.0 g), and the mixture was heated up to 65° C., and maintained at the same temperature for 2 hours. Thus, the aqueous solution (290.5 g) of diammonium 4-chloro-2-fluoro-5-hydroxyphenylhydrazine-N,N'-disulfonate was obtained.

The obtained aqueous solution of diammonium 4-chloro-2-fluoro-5-hydroxyphenylhydrazine-N,N'-disulfonate was dropwise added to 35% hydrochloric acid (361.5 g, 3.470 moles) over 2 hours while cooling hydrochloric acid at 10° C., and further reacted at the same temperature for 4 hours to obtain a reaction mixture (648.4 g) (93.5% of 4-chloro-2-fluoro-5-hydroxyphenylhydrazine; 0.6% of the dechlorinated compound (by-product); LC area percentages). After the filtration of the reaction mixture, the residue was dried to obtain a pale pink solid mixture containing 4-chloro-2-fluoro-5-hydroxyphenylhydrazine hydrochloride (44.4 g) (96.5% of 4-chloro-2-fluoro-5-hydroxyphenylhydrazine; no dechlorinated compound being detected; LC area percentages).

According to LC-IS analysis, the yield of 4-chloro-2-fluoro-5-hydroxyphenylhydrazine was 88.0% based on 4-chloro-$C_{1-2}$-fluoro-5-hydroxyaniline.

The water contained in the reaction mixture was 440 g, and thus the amount of the inorganic acids in the reaction system was 7.9 moles per 1 kg of water.

EXAMPLE 4

The aqueous solution of disodium 4-chloro-2-fluoro-5-hydroxyphenylhydrazine-N,N'-disulfonate (2610.6 g) was prepared in the same manner as in Example 1 except that 10% hydrochloric acid (896.4 g), 4-chloro-2-fluoro-5-hydroxyaniline (132.9 g, content: 99.6%, 0.819 mole), a 35% aqueous solution of sodium nitrite (169.6 g), water (1084.5 g), sodium sulfite (326.2 g) and 96% sulfuric acid (14.8 g) were used.

The obtained aqueous solution (200.0 g) of disodium 4-chloro-2-fluoro-5-hydroxyphenylhydrazine-N,N'-disulfonate was cooled to 10° C. Then, to the cooled solution, 96% sulfuric acid (178.5 g, 1.747 moles) was charged at 10° C. over 30 minutes, and reacted at 15° C. for 2 hours to obtain a reaction mixture (377.9 g) (90.4% of 4-chloro-2-fluoro-5-hydroxyphenylhydrazine; 1.2% of the dechlorinated compound (by-product); LC area percentages). After the filtration of the reaction mixture, the residue was washed with saturated brine (115.7 g) and dried to obtain an ash gray solid mixture containing 4-chloro-2-fluoro-5-hydroxyphenylhydrazine sulfate. (21.2 g) (96.2% of 4-chloro-2-fluoro-5-hydroxyphenylhydrazine; 0.3% of the dechlorinated compound (by-product); LC area percentages).

According to LC-IS analysis, the yield of 4-chloro-2-fluoro-5-hydroxyphenylhydrazine was 85.5% based on 4-chloro-2-fluoro-5-hydroxyaniline.

The water contained in the reaction mixture was 161 g, and thus the amount of the inorganic acids in the reaction system was 10.9 moles per 1 kg of water.

The results of Examples 1–4 are summarized in Table 3.

TABLE 3

| | Inorganic acid | Amount of Inorganic acid per 1 kg of water in reaction system (moles) | Yield[1] of phenyl-hydrazines (%) |
|---|---|---|---|
| Example 1 | Hydrochloric acid | 6.5 | 89.3 |
| Example 2 | Hydrochloric acid | 6.9 | 89.4 |
| Example 3 | Hydrochloric acid | 7.9 | 88.0 |
| Example 4 | Sulfuric acid | 10.9 | 85.5 |

Note:
[1]A yield based on the raw material aniline derivative.

What is claimed is:

1. A process for the preparation of a phenylhydrazine or an inorganic acid salt thereof of the formula (1):

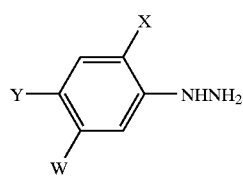

(1)

wherein X is a hydrogen atom or a halogen atom;
Y is a halogen atom; and
W is a hydrogen atom or —ZR in which Z is an oxygen atom or a sulfur atom, and R is a hydrogen atom, a $C_1$–$C_6$ alkyl group, a $C_1$–$C_6$ haloalkyl group, a $C_3$–$C_6$ cycloalkyl group, a benzyl group, a $C_3$–$C_6$ alkenyl group, a $C_3$–$C_6$ haloalkenyl group, a $C_3$–$C_6$ alkynyl group, a cyano-$C_1$–$C_6$ alkyl group, a $C_2$–$C_8$ alkoxyalkyl group, a $C_2$–$C_8$ alkylthioalkyl group, a carboxy-$C_1$–$C_6$ alkyl group, ($C_1$–$C_8$ alkoxy) carbonyl-$C_1$–$C_6$ alkyl group, a [($C_1$–$C_4$ alkoxy)-$C_1$–$C_4$ alkoxy] carbonyl-$C_1$–$C_6$ alkyl group, ($C_3$–$C_8$ cycloalkoxy) carbonyl-$C_1$–$C_6$ alkyl group or a [($C_1$–$C_6$ alkoxy) carbonyl-$C_1$–$C_6$ alkyl]oxycarbonyl-$C_1$–$C_6$ alkyl group;
said method consisting essentially of the step of hydrolyzing a phenylhydrazine derivative of the formula (2):

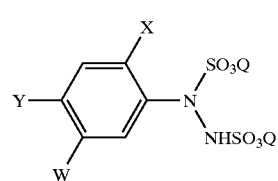

(2)

in the presence of water and an inorganic acid, wherein the concentration of the inorganic acid is at least 6 moles per 1 kg of water in a reaction system;
wherein X, Y and W of formula (2) are the same as defined in formula (1), and the Q groups are the same or different from each other and represent a hydrogen atom, an ammonium group or an alkali metal atom.

2. The process according to claim 1, wherein said phenylhydrazine derivative of the formula (2) is prepared by diazotizing an aniline derivative of the formula (3):

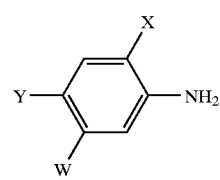

(3)

and then reacting the obtained diazonium salt with at least one compound selected from the group consisting of sulfurous acid, sulfite salts and hydrogensulfite salts.

3. The process according to claim 1, wherein a phenylhydrazine or an inorganic acid salt thereof of the formula (1) is filtrated after hydrolysis.

4. The process according to claim 1, wherein the amount of said inorganic acid is from 4 to 50 moles per one mole of said phenylhydrazine derivative of the formula (2).

5. The process according to claim 1, wherein X is a halogen atom.

6. The process according to claim 5, wherein W is —ZR.

* * * * *

UNITED STATES PATENT AND TRADEMARK OFFICE
CERTIFICATE OF CORRECTION

PATENT NO. : 6,852,890 B1
DATED : February 8, 2005
INVENTOR(S) : Kazuyuki Tanaka et al.

It is certified that error appears in the above-identified patent and that said Letters Patent is hereby corrected as shown below:

Column 2,
Line 66, the phrase reading "$C_3$-$C_6$ cycloalkyl group" should read as -- $C_3$-$C_8$ cycloalkyl group --.

Column 9, line 54 to Column 10, line 1,
The phrase reading "$C_3$-$C_6$ cycloalkyl group" should read as -- $C_3$-$C_8$ cycloalkyl group --.

Signed and Sealed this

Twelfth Day of July, 2005

JON W. DUDAS
*Director of the United States Patent and Trademark Office*